United States Patent [19]

Koledin et al.

[11] Patent Number: 4,589,407
[45] Date of Patent: May 20, 1986

[54] SPINE IMMOBILIZER

[75] Inventors: Michael J. Koledin, El Cajon; Geoffrey C. Garth, Long Beach, both of Calif.

[73] Assignee: National Medical Distributors, El Cajon, Calif.

[21] Appl. No.: 608,377

[22] Filed: May 9, 1984

[51] Int. Cl.$^4$ .............................................. A61F 5/04
[52] U.S. Cl. .................................. 128/87 R; 128/88; 128/134
[58] Field of Search ............... 128/78, 85, 87 R, 87 B, 128/88, 90, 93, 134; 229/37 E, 23 A

[56] References Cited

U.S. PATENT DOCUMENTS

| 2,409,195 | 10/1946 | Crawford | 128/87 R |
| 2,502,384 | 3/1950 | Loth | 229/23 A |
| 3,620,211 | 11/1971 | Goodell | 128/78 X |
| 4,209,011 | 6/1980 | Peck et al. | 128/87 R |
| 4,211,218 | 7/1980 | Kendrick | 128/87 R |

Primary Examiner—Richard J. Apley
Assistant Examiner—Alan W. Cannon
Attorney, Agent, or Firm—Fulwider, Patton, Rieber, Lee & Utecht

[57] ABSTRACT

A spine immobilizer particularly adapted for rendering an accident victim's head and upper body immobile. The spine immobilizer in a preferred form is made of a sheet of corrugated cardboard including a multilayer spine panel to resist longitudinal bending, laterally extending head panels bendable into position adjacent the sides of the person's head, laterally extending body panels bendable into conformity with the person's upper body, and straps and fastening assemblies for securing the body panels in position. The immobilizer includes box sections providing increased resistance to longitudinal bending, one formed by laterally extending stiffener panels having free ends arrangable in overlying relation, and others formed by the strap arrangement. Features include laterally adjustable carrying handles, and slot and strap configurations which reduce tearing of the cardboard.

13 Claims, 5 Drawing Figures

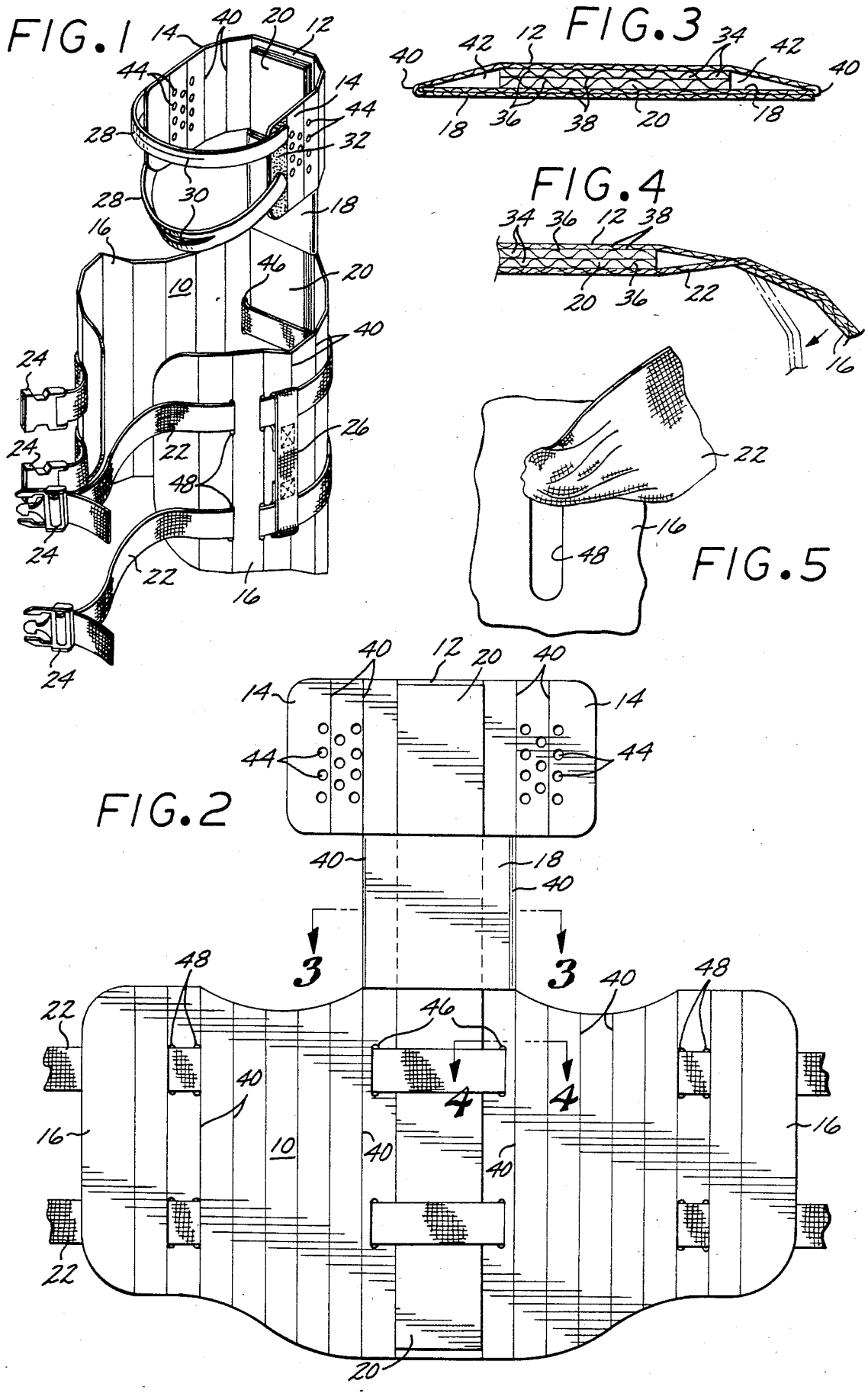

SPINE IMMOBILIZER

BACKGROUND OF THE INVENTION

1. Field of the Invention

The present invention relates to spine immobilizers and particularly to spine immobilizers adapted to be fitted to an injured person before the person is moved from an accident site.

2. Description of the Prior Art

Immobilization of a person prior to removal from an accident site is important to prevent possible injury to the spine or aggravation of injuries already suffered. An unwieldy wooden back board has been used for years for this purpose but the device is impractical to fit to a person still located in an accident vehicle. More recently, devices have been developed which can be fitted and strapped to the accident victim prior to removal of the victim from the vehicle. One such device is characterized by a combination of cushioning foam material, an overlying sheet of solid plastic material, a protective cover of nylon fabric, and an integral or insertable longitudinal stiffener in the spine area. Except for the single stiffener this device is quite flexible. There is considerable evidence indicating that resistance to longitudinal bending should be present throughout a spine immobilizer.

Another device of the prior art does not provide immobilization of the head of an accident victim and requires a separate cervical collar for this purpose.

Yet another device of the prior art is laterally flexible for fitting about the injured person, and is rendered longitudinally stiff by a plurality of elongated stiffeners individually fitted within sleeves stitched into the otherwise flexible material of the device.

The primary objection to these and other spine immobilizers presently available for emergency use is their relatively high cost. Both the materials used and the manner of their fabrication raise the costs to the point that ambulances and similar emergency vehicles may have only one of the devices on hand, posing a serious problem when an accident involves more than one person.

SUMMARY OF THE INVENTION

According to the present invention, a spine immobilizer is provided which is made of low cost materials like corrugated cardboard to make it available to low budget emergency vehicle operations. The materials are light in weight, can be folded almost flat, and are inherently longitudinally stiff throughout.

The present spine immobilizer includes vertically scored head and body panels adapted to bend conformably to the victim's head and body, respectively, being held in position by suitable straps or the like. In one embodiment the location of the strap openings, and their size and location relative to the straps, facilitate lateral bending of the body panels. A carrying handle arrangement enables carriage of the accident victim in a sitting posture without failure or tearing of the cardboard or other material used.

The immobilizer includes a vertical spine stiffener and a hollow box section formed by a pair of stiffener panels foldable over the spine stiffener to provide further resistance to longitudinal bending. Other box sections are formed by the strap arrangement.

Other objects and features of the invention will become apparent from consideration of the following description taken in connection with the accompanying drawings.

BRIEF DESCRIPTION OF THE DRAWINGS

FIG. 1 is a perspective view of the present spine immobilizer and its general conformation when applied to an accident victim;

FIG. 2 is a plan view of the spinal immobilizer of FIG. 1 laid flat;

FIG. 3 is a view taken along the line 3—3 of FIG. 2;

FIG. 4 is a view taken along the line 4—4 of FIG. 2; and

FIG. 5 is an enlarged view of one of the webbing slots, illustrating the manner in which the webbing-like material of the cross straps tends to bunch up in the upper portion of such a slot when the spine immobilizer is used to carry an accident victim in a sitting posture.

DESCRIPTION OF THE PREFERRED EMBODIMENT

Referring now to the drawings, there is illustrated a spine immobilizer according to the present invention comprising, generally, an integral sheet 10 which includes a central, longitudinally extending spine panel 12; a pair of head panels 14 extending laterally on opposite sides of the spine panel 12; a pair of body panels 16 below the head panels 14 and extending laterally on opposite sides of the spine panel 12; a pair of stiffener panels 18 located between the head panels 14 and body panels 16 and extending laterally on opposite sides of the spine panel 12; and longitudinally extending stiffening means 20 adjacent to and integral with the spine panel 12 to increase the resistance of the spine panel 12 to longitudinal bending.

The immobilizer further comprises a pair of cross straps 22 made of nylon fabric or similar webbing-like material and mounted to the body panels 16. The straps 22 carry buckle assemblies 24 at their free extremities to facilitate lateral bending of the body panels 16 in conforming relation to a wearer's body, and attachment together of the body panels 16 to constrain the wearer's body against lateral movement.

The particular type and configuration of the buckle assemblies 24 is not important to the present invention, the type illustrated having interconnecting receptacle and bayonet portions. Each bayonet portion is spring biased for latching within its mating receptacle, release being accomplished by a deliberate pressure at both sides of the assembly.

The head panels 14 are laterally bendable into adjacent relation with opposite sides of a person's head to constrain the person's head against lateral movement. The free extremities of the panels 14 are secured in position by elongated, horizontally oriented forehead and chin straps 28. The straps 28 are made of foam material and each includes a horizontal, centrally located slit 30.

The forehead strap is adapted to overlie the wearer's forehead, and the chin strap extends across the chin, with the chin extending through the slit 30. The unused slit 30 in the forehead strap is provided to make the straps interchangeable.

The free end of the straps 28 are attached by a hook and barb "Velcro" arrangement. The foam material of the straps 28 constitutes the barb portion of the Velcro fastener, and a pair of Velcro hook type material strips 32, only one of which is illustrated, are adhered to the free ends of the head panels 14. The straps 28 readily adhere to the strips 32 to firmly secure the head panels 14 in position.

As best seen in FIGS. 3 and 4, the sheet 10 is sandwich material, including a plurality of longitudinally extending cells 34 defined by longitudinally extending walls 36 disposed between parallel outer layers 38. This makes the sheet 10 relatively light in weight and highly resistant to longitudinal bending. Typical materials providing these characteristics are conventional corrugated cardboard and an extruded plastic material known in the trade as COROPLAST. This plastic material is discussed in U.S. Pat. No. 4,209,011, issued June 24, 1980 for "Disposable Splint". Use of cardboard material is preferred because it is relatively inexpensive and readily available. If desired, it can be coated with wax, or plastic resins or the like to render it waterproof and resistant to staining by blood and other body fluids. This extends the service life significantly.

Although corrugated cardboard is a preferred material, other materials having high resistance to longitudinal bending could be used. Solid, non-sandwich materials such as sheet plastic or similar materials with longitudinal stiffeners suggest themselves, particularly integral stiffeners defined by the material configuration. The configuration could provide corrugations, or box sections or the like.

The head panels 14 and body panels 16 each include a plurality of laterally spaced, longitudinally extending scoring or fold lines 40 which facilitate lateral bending of the panels into the configuration illustrated in FIG. 1.

Because it is of such critical importance to immobilize an accident victim's spine against any longitudinal bending, the spine panel 12 is further provided with the stiffening means 20. In the present embodiment the means 20 conveniently takes the form of a stack of rectangular, longitudinally extending sections made of the same material as sheet 10. The superposed sections are glued or otherwise adhered to the spine panel 12 and to each other to form the built up stiffening means seen in FIGS. 3 and 4. Of course, other stiffening elements could be provided in the form of slats, rods, built up coatings or layers of stiffening material, or the like.

Even greater resistance to longitudinal bending is provided by the pair of stiffener panels 18. Although not illustrated in their original folded out or flat form, the stiffener panels 18 in their flat form extend laterally of the spine panel 12 and each includes a fold line 40. Each of these fold lines 40, as seen in FIGS. 2 and 3, is located laterally outwardly from the adjacent side edge of the longitudinal stiffening means 20, the distance approximating that between a pair of the fold lines 40.

The structure seen in FIG. 3 is formed by folding one stiffener panel 18 over at the fold line 40 just described, and across the stiffening means 20. This forms a triangular cell 42. Next, the other stiffener panel 18 is folded over the first to form another cell 42. The cells 42 and adjacent walls define a form of box section very resistant to longitudinal bending. The term "box section" as used here and in the appended claims is intended to denote any section defined by spaced members, such as the panels 18 and the oppositely located spine panel 12, which are spaced apart and secured together by other elements, such as the stiffening means 20 and the inclined portions of the panels 18 located inwardly of the fold lines 40 seen in FIG. 3.

The free extremities of the stiffener panels 18 are fixed in position, being glued or otherwise adhered to each other and to the upper surface of the longitudinal stiffening means 20.

A feature of the head panels 14 is the provision of openings or apertures 44 for location adjacent the ears of the accident victim. This not only permits the victim to hear those around him or her, but also would reveal bleeding from the ears, a sign of a possible skull fracture.

The cross straps 22 are horizontally oriented and longitudinally spaced apart, as best illustrated in FIGS. 1 and 2. Each cross strap 22 is disposed through a plurality of laterally spaced apart longitudinally extending webbing slots 46 and 48. The slots 48 are located in approximate alignment with fold lines 40 located adjacent the free ends of the body panel 16. On the other hand, the slots 46 are located immediately adjacent and on opposite sides of the centrally located longitudinally stiffening means 20. Each slot 46 is located between the side edge of the longitudinal stiffening means 20 and next to the adjacent fold line 40. With this arrangement when the cross straps 22 are brought around and over the body of the injured person, tension on the cross straps 22 will desirably initiate a bending of the body panels 16 at the fold lines 40 located adjacent the slots 46.

This location of the initial bending not only provides close conformity of the body panels 16 to the person's body, as compared to a random bending of the body panels 16 at other fold lines 40 but, more importantly, a pair of longitudinal stiffening structures or box sections are defined by the straps. Each box section is defined on the inner side by the strap and the upper surface of the stiffening means 20, and on the outer side by the spine panel 12. The adjacent portions of the body panels 16 and the stiffening means 20 space apart the inner and outer sides and form the lateral sides of each box section.

The two box sections just described, together with the box section formed in part by the stiffener panels 18, provide three relatively rigid box sections at three different positions along the length of the spine panel 12.

The longitudinally oriented carrying straps 26 include end loops disposed about the adjacent cross straps 22. The absence of any slots between the slots 46 and 48 enables lateral sliding of the carrying straps 26 along the cross straps 22 whereby the weight of an injured person can be more effectively distributed for lifting. Although the handles 26 are normally utilized to carry an injured person in a horizontal position, they are also used, upon initial removal of an injured person from a vehicle, to extricate and carry the person in a vertical or seating posture. When the carrying straps 26 are used to carry the injured person in a seating posture, the webbing-like material of the cross straps 22 tends to bunch up in the upper portions of the slots 48. This is desirable because it reduces tearing and tear propagation of the material of the panel adjacent the upper portions of the slots 48, as best seen in FIG. 5. To promote such bunching up, the slots 48 are each made sufficiently wider than the thickness of the webbing-like material of the straps 22 that the material has room to bunch up. The proper ratio of slot size to strap thickness, and the proper strap flexibility can easily be established after a few trials, as will be apparent.

Tear propagation at the slot ends can also be reduced by providing larger radius ends (not shown) for better stress distribution.

By virtue of the lightweight and relatively inexpensive construction of the present spine immobilizer, it has been found that it can be manufactured at a cost low enough to make it available to all levels of health care facilities. The cost is sufficiently low, in fact, that it may well develop to be a one-use, throwaway item, except perhaps for salvaging of the fastener assemblies.

Various modifications and changes may be made with regard to the foregoing detailed description without departing from the spirit of the invention.

We claim:

1. A spine immobilizer comprising:
 a sheet of material including a plurality of longitudinally extending cells defined by a plurality of longitudinally extending walls disposed between outer layers whereby said sheet is relatively light in weight and resistant to longitudinal bending, said sheet further including a central, longitudinally extending spine panel; a pair of head panels extending laterally on opposite sides of said spine panel; a pair of body panels extending laterally on opposite sides of said spine panel said body panels including a pair of longitudinally spaced apart sets of laterally spaced apart, longitudinally extending slots; a pair of stiffener panels in overlying relation each with respect to the other, each of said stiffener panels secured to an opposing edge of said spine panel, said stiffener panels extending laterally on opposite sides of said spine panel and located between said head panels and said body panels; and longitudinally extending stiffening means adjacent to and integral with said spine panel and having a predetermined thickness greater than the thickness of said spine panel so as to be operative to increase the resistance of said spine panel to longitudinal bending, said head panels having laterally spaced apart, longitudinally extending fold lines to facilitate lateral bending of said head panels into adjacent relation with opposite sides of a person's head whereby the free extremeties of said head panels can be secured together to constrain a person's head against lateral movement, said body panels having laterally spaced apart, longitudinally extending fold lines to facilitate lateral bending of said body panels in-conforming relation to a person's body to constrain the body against lateral movement, the free extremities of said stiffener panels being secured together in overlying relation to said spine panel to define enclosed spaces forming a box section resistant to longitudinal bending; and
 fastening means carried by said body panels and including a pair of cross straps extending through said slots of said sets, respectively, for securement together of the free extremities of said cross straps to secure said body panels in said conforming relation and wherein said stiffening means is secured to and projects above the inner surface of said spine panel, certain of said webbing slots are located adjacent said stiffening means, and said pair of cross straps extends across said stiffening means whereby tightening of said cross straps forms a cross section providing longitudinal stiffening, each said cross section being defined by said stiffening means, said spine panel and adjacent portions of said body panels, and one of said cross straps.

2. A spine immobilizer according to claim 1 wherein said material of said sheet is corrugated cardboard.

3. A spine immobilizer according to claim 1 wherein said material of said sheet is extruded plastic material.

4. A spine immobilizer according to claim 2 wherein said fold lines are scoring lines.

5. A spine immobilizer according to claim 1 wherein said head panels include a plurality of apertures enabling inspection of the wearer's ears.

6. A spine immobilizer according to claim 1 wherein said stiffening means comprises a plurality of layers made of the same material of which said sheet is made, and adhered together to the inner surface of said spine panel.

7. A spine immobilizer according to claim 1 including a pair of longitudinally oriented carrying straps, each having end loops disposed about said cross straps, respectively, whereby said carrying straps are laterally slidable along said cross straps between adjacent ones of said slots thereby to enable the wearer of said spine immobilizer to be carried.

8. A spine immobilizer according to claim 1 wherein said carrying straps are made of flexible webbing-like material, and said slots are each made enough wider than the thickness of said webbing-like material that said webbing-like material tends to bunch up in the upper portions of said slots during carriage of the wearer in a sitting posture, thereby reducing tearing and tear propagation of the material of said sheet adjacent said upper portions of said slots.

9. A spine immobilizer comprising:
 material means resistant to longitudinal bending and including a central, longitudinally extending spine portion;
 a pair of head portions extending laterally on opposite sides of said spine portion;
 a pair of body portions extending laterally on opposite sides of said spine portion; reinforcing means adjacent said spine portion and including a pair of stiffener panels in overlying relation each with respect to the other, each of said stiffener panels secured to an opposing edge of said spine portion, said stiffener panels extending laterally on opposite sides of said spine portion and located between said head portions and said body portions, the free extremities of said stiffener panels being secured together in overlying relation to said spine portion to define enclosed spaces forming a box section resistant to longitudinal bending; and
 longitudinally extending stiffening means adjacent said spine portion and operative to increase the resistance of said spine portion to longitudinal bending, said head portions being laterally bendable into adjacent relation with opposite sides of a person's head whereby the free extremities of said head portions can be secured together to constrain a person's head against lateral movement, said body portions being laterally bendable into conforming relation to a person's body to constrain a person's body against lateral movement.

10. A spine immobilizer according to claim 9 wherein said spine portion, head portions and body portions are panel sections of said material means, and said head portions and body portions include longitudinal fold lines to facilitate their lateral bending.

11. A spine immobilizer according to claim 9 wherein said body portions include a first pair of webbing slots on opposite sides of and spaced laterally from said spine portion, and said reinforcing means comprises a first cross strap extending through said slots and tensionable to maintain said body portions in said conforming relation and to form a longitudinally stiff box section defined by said first cross strap, said spine portion, and the adjacent sections of said body portions which are bent out of the plane of said spine portion.

12. A spine immobilizer according to claim 11 and including a second cross strap and a second pair of webbing slots longitudinally spaced from said first cross strap and said second pair of webbing slots whereby the intervening sections of said spine portion and the adjacent sections of said body portions form a box section whose shape is maintained by said first and second cross straps.

13. A spine immobilizer comprising:
material means resistant to longitudinal bending and including a central, longitudinally extending spine portion;
a pair of head portions extending laterally on opposite sides of said spine portion;
a pair of body portions extending laterally on opposite sides of said spine portion; said head portions being laterally bendable into adjacent relation with opposite sides of a person's head whereby the free extremities of said head panels can be secured together to constrain a person's head against lateral movement, said body portions being laterally bendable into conforming relation to a person's body to constrain a person's body against lateral movement, said body portions including a pair of longitudinally spaced apart sets of laterally spaced apart, longitudinally extending webbing slots;
a pair of stiffener panels located between said body and head portions, said stiffener panels in overlying relation each with respect to the other, each of said stiffener panels secured to an opposing edge of said spine portion;
fastening means comprising a pair of cross straps extending through said slots of said sets, respectively, for securement together of the free extremities of said cross straps to maintain said conforming relation; and
a pair of longitudinally oriented carrying straps, each having end loops disposed about said cross straps, respectively, whereby said carrying straps are laterally slidable along said cross straps adjacent the forward ones of said slots thereby tending to orient the wearer of said spine immobilizer in a horizontal position for transport.

* * * * *